Figure 1:
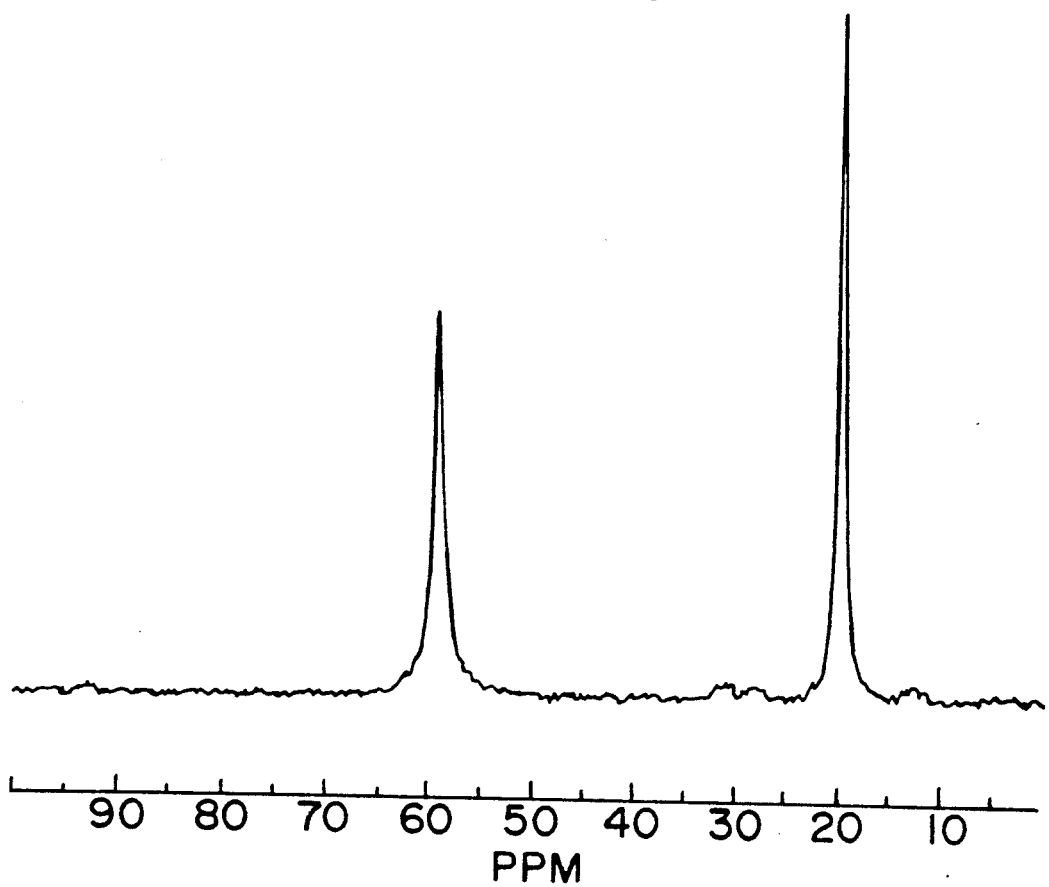

United States Patent [19]

Smith et al.

[11] Patent Number: 5,262,573
[45] Date of Patent: Nov. 16, 1993

[54] HALOMAGNESIUM HYDROCARBYLOXIDE COMPOSITION AND PROCESS FOR PREPARATION

[75] Inventors: Gregory M. Smith, Danbury, Conn.; Richard J. Amata, Tarrytown, N.Y.; Charles F. Tirendi, Mohegan Lake; Elliot I. Band, North Tarrytown, both of N.Y.

[73] Assignee: Akzo nv, Arnhem, Netherlands

[21] Appl. No.: 741,013

[22] Filed: Aug. 6, 1991

[51] Int. Cl.$^5$ .................. C07C 31/30; C07C 29/70
[52] U.S. Cl. ...................... 568/851; 568/652; 568/715; 568/716; 568/834; 568/844; 568/852
[58] Field of Search .............. 568/672, 700, 652, 715, 568/716, 834, 841, 844, 851, 852

[56] References Cited

U.S. PATENT DOCUMENTS

| | | |
|---|---|---|
| 4,727,051 | 2/1988 | Breen et al. ............ 568/851 |
| 4,792,640 | 12/1988 | Mehta ................. 568/851 |
| 4,820,879 | 4/1989 | Mehta ................. 568/851 |
| 5,023,385 | 6/1991 | Wang et al. ........... 568/851 |

Primary Examiner—Werren B. Lone
Attorney, Agent, or Firm—Richard P. Fennelly; Louis A. Morris

[57] ABSTRACT

A substantially pure, chemically distinct halomagnesium alkoxide compound is formed by reaction of a dihydrocarbylmagnesium compound with a compound which will replace an hydrocarbyl functionality thereon with an hydrocarbyloxy functionality and thereafter reacting the resulting product with a compound which replaces the other hydrocarbyl functionality with a halogen functionality, such as chlorine. The $^{13}C$ nuclear magnetic resonance spectrum of the product exhibits no more than one strong, narrow absorption peak for each chemically inequivalent carbon atom in the hydrocarbyloxy ligand of the compound.

21 Claims, 1 Drawing Sheet

HALOMAGNESIUM HYDROCARBYLOXIDE COMPOSITION AND PROCESS FOR PREPARATION

BACKGROUND OF THE INVENTION

This invention relates to the problem of preparing support materials useful as components of olefin polymerization catalysts, and the process used to prepare them. In particular, it relates to the preparation of insoluble catalyst support materials containing magnesium, halide and hydrocarbyloxide in well defined ratios. Most particularly, this invention concerns the preparation of substantially pure solid halomagnesium hydrocarbyloxide catalyst support materials with well defined and uniform composition.

The term "hydrocarbyloxide" is intended to cover structures of the formula —OR where R is "hydrocarbyl", i.e., a moiety formed by the removal of hydrogen from a hydrocarbon, e.g. alkyl, aryl and alkylaryl. There are many examples in the prior art of olefin polymerization catalysts obtained by combining a component comprising magnesium halide and a titanium halide with an activating organoaluminum compound. The polymerization activity, stereospecificity, and comonomer incorporation characteristics of such compounds may be manipulated in various ways. In some cases this is accomplished by controlling the particular composition of the magnesium halide, for instance, by including some alkoxy ligands in the magnesium halide compound, or by halogenating a particular magnesium dialkoxide to prepare the magnesium halide. Magnesium halide-supported catalysts for the polymerization of olefins prepared by halogenating a magnesium alkoxide are described in U.S. Pat. Nos. 4,400,302 and 4,414,132 to Goodall, et. al., for example. Since the morphology of the polymer is generally controlled by that of the catalyst, much effort has been expended in attempting to control the morphology of such catalysts.

Examples of catalyst components that are prepared in processes employing materials containing magnesium, halide and hydrocarbyloxide can be found in European Patent Publication No. 301,894. This patent document illustrates the preparation of catalyst components with specific useful polymerization characteristics (comonomer incorporation, polymer crystallinity, etc.) by employing these materials.

In view of the above considerations, the nature of the magnesium-containing component of a polymerization catalyst composition, and the process used to prepare it are very important. The prior art includes many strategies for the preparation of magnesium, halide and hydrocarbyloxide containing polymerization catalyst support materials. Most of these strategies are based on the work of Turova and Turevskaya (Journal of Organometallic Chemistry, vol. 42, (1972), pp 9–17). Turova et al. suggested thermolysis of $Mg(OR)_2$ and $MgX_2$ mixtures (X=halogen; R, R'=alkyl, aryl, etc), eq. (1), or the alcoholysis of Grignard reagents, eq. (2):

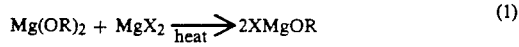

$$Mg(OR)_2 + MgX_2 \xrightarrow{heat} 2XMgOR \qquad (1)$$

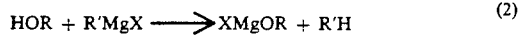

$$HOR + R'MgX \longrightarrow XMgOR + R'H \qquad (2)$$

Subsequent work has varied from this earlier work in certain details, such as in U.S. Pat. Nos. 4,814,313 to Murata et. al. and 4,220,554 to Scata et. al. where Grignard reagents were formed in situ and then reacted with alkoxy ligand sources, eq. (3).

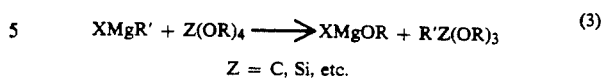

$$XMgR' + Z(OR)_4 \longrightarrow XMgOR + R'Z(OR)_3 \qquad (3)$$

Z = C, Si, etc.

Another minor variation can be found in U.S. Pat. No. 4,820,879 to Mehta, who uses HX (eq. (4)) as the halogen ligand source, rather than $MgX_2$ as in eq. (1).

$$Mg(OR)_2 + HX \rightarrow XMgOR + HOR \qquad (4)$$

In the method of eq. (3), halide is present before the hydrocarbyloxide is formed, and may or may not be present in the desired ratio to magnesium because of the Schlenk equilibrium. In the method of eq. (4), the halogen ligand source must react with only part of the hydrocarbyloxy ligands present, in order to get the desired product stoichiometry, and the extent of reaction is difficult to control.

Common concerns in the preparation of insoluble solid materials are the issues of uniformity, purity, and composition. Catalyst support materials are substances that may be categorized as either "ionic structures" or "covalent infinite arrays". In these cases it is not always a simple matter to establish the uniformity and purity of a material. Although the above strategies (eq. (1) through eq. (4)) purport to prepare solid compounds such as "XMgOR", they are not supported by examples where the chemical and spectroscopic characterization of the product demonstrates that it is a uniform solid of well defined composition with established purity. (Terminology taken from *Advanced Inorganic Chemistry*, 5th edition, by F. A. Cotton, and G. Wilkinson: John Wiley and Sons; New York, 1988). In many cases it is possible, and even likely, that the product was actually a mixture, e.g. of $MgX_2$ and $Mg(OR)_2$, that merely had the correct average composition. In all cases where there was spectroscopic characterization sufficient to differentiate between a solid of uniform composition and purity, and a mixture (e.g. U.S. Pat. Nos. 4,820,879 and 4,792,640 to Mehta), mixtures were found.

DESCRIPTION OF THE INVENTION

This invention employs a novel, selective, step-wise, process that exploits a) the high reactivity of magnesium hydrocarbyl groups toward hydrocarbyloxy ligand sources, and b) the difference in reactivity between magnesium hydrocarbyl ligands and magnesium hydrocarbyloxy ligands in reactions with halogen ligand sources to prepare solids of uniform composition and purity with empirical formulae such as XMgOR where, X is halogen and OR is a hydrocarbyloxy group containing from 1 to 20 carbon atoms. Furthermore, this novel process permits the preparation of novel solids of uniform composition and purity having empirical formulae: $X_{2-z}Mg(OR)_z$ where $0 \leq z < 2$; or $X_{N(2-z)}Mg_N(OR)_{Nz}$ where $0 \leq z < 2$ and N is a conveniently chosen multiplier to reduce rational numbers to integers, where the ratios of halide to magnesium (N(2−z):N) and alkoxide to magnesium (Nz:N) are not always 1:1.

The strategy used in regard to the present process is to start with a magnesium compound containing two very reactive groups bound to magnesium, such as hydrocarbyl groups, and introduce the hydrocarbyloxy ligand first. A controlled amount of hydrocarbyloxy ligand is bound to the magnesium by introducing an oxygen-containing compound which can react with the reactive groups on the magnesium to produce the desired magnesium hydrocarbyloxy ligand. This reaction should be chosen so that the oxygen compound is completely consumed, which will insure that the amount of magnesium hydrocarbyloxy bonds can be precisely controlled. The product from this reaction thus contains an amount of a reactive group bound to magnesium, and an amount of less reactive hydrocarbyloxy ligands bound to magnesium. For example:

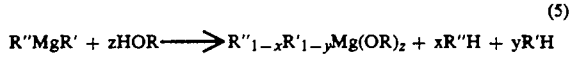
(5)

R, R', R" = same or different hydrocarbyls;
$x + y = z$;
$0 \leq x < 1$;
$0 \leq y < 1$.

Because the magnesium-hydrocarbyloxy ligand bond is relatively less reactive than the remaining reactive group, the product from this reaction can, with or without isolation, be combined with a halogen ligand source that reacts preferentially with the remaining reactive groups:

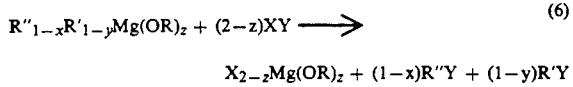
(6)

X = halogen;
Y = e.g. halogen, pseudohalogen, $X_3Si$, or similar moiety bound to halogen;
other groups and terms as in eq. (5)

A more specific example of the foregoing is supplied by the following two equations:

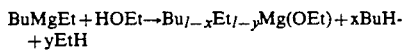
(7)

$x + y = 1$
$0 \leq x < 1$
$0 \leq y < 1$.

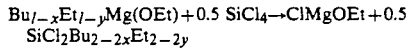
(8)

Note that in this case, since each silicon can supply two halogen ligands, ½ mole of halogenating reagent is required, instead of 1 mole.

If the reactivity of the halogen ligand source is such that it also reacts to some extent with the less reactive hydrocarbyloxy ligand, a controlled excess of the hydrocarbyloxy ligand may be added in the first step, eqs. (5), (7), as well as a controlled excess of halogenating agent in the second step, eq. (6), (8).

Examples of reactive groups useful in the initial magnesium compound include $C_{1-20}$ saturated alkyl groups, $C_{6-20}$ aryl groups, or $C_{7-20}$ alkylaryl groups. Examples of hydrocarbyloxy groups that could be formed on magnesium include $C_{1-20}$ alkylalkoxides, $C_{6-20}$ arylalkoxides, and $C_{7-20}$ alkylarylalkoxides. Examples of compounds suitable for use as the hydrocarbyloxy ligand source include $C_{1-20}$ saturated alcohols, $C_{6-20}$ arylalcohols, or $C_{7-20}$ alkylaryl alcohols. Other oxygen-containing organic molecules could also be used, including epoxides, ketones, aldehydes, acetals, carbonates, or orthoformates. Inorganic or organometallic hydrocarbyloxide donors, such as $M(OR)_4$, where M = Si, Ge, or Sn, or hydrocarbyl-hydrocarbyloxy compounds such as $R_{4-x}M(OR)_x$ with $0 < x \leq 4$ might also be employed.

Examples of compounds useful as halogen donors includes the acid halides: HX, elemental halogens: $X_2$, and metal halides such as $MX_xY_{4-x} 0 < x \leq 4$ where M = C, Si, Ge, or Sn, and Y = any group bound to M through a single bond. Other potential halogen donors include organic acid halides such as RC(O)X, chloroformates such as ROC(0)X, acid halides of main group oxygen acids, such as $SOX_2$ and $POX_3$. Main group halo compounds such as $PX_3$, $PX_5$, or $BX_3$ could also be used.

In addition to the features outlined elsewhere in this text, it is important that the reaction between the hydrocarbyloxy ligand source and the dihydrocarbyl magnesium yield a homogenous solution as a reaction product, and it is preferred that any reaction by-products be easily removed, or else inert in subsequent steps. It is desirable, but not mandatory that the reactivity of the halogen source be such that the hydrocarbylmagnesium hydrocarbyloxide and the halogen source can be mixed without obvious reaction at low temperature, and then brought to a temperature where a controlled reaction occurs. By-products from the halogenation step should be easily removed from the product.

In a preferred embodiment of this invention, a soluble dihydrocarbyl magnesium is reacted with alcohol to form hydrocarbyloxy groups and inert saturated or aromatic hydrocarbons to give a soluble product in an inert saturated or aromatic hydrocarbon solvent. This product is then halogenated with a compound $R_{4-6x}KC_x$ compound with R = hydrocarbyl, M = C, Si, Ge or Sn, and $0 < x \leq 4$. In the most preferred embodiment of this invention, a primary saturated alcohol and silicon tetrachloride are used.

Some critical aspects of this reaction involve magnesium-ligand reactivity. In the first step, it is critical that the ligands initially bound to magnesium be reactive toward the hydrocarbyloxy ligand source. In the second step, it is critical that the remaining initial ligands be more reactive than the hydrocarbyloxy ligand toward the halogen ligand source. Finally, it is important to know the reactivity of the halogen ligand source so that one will be able to supply the desired amount of halogen ligand. In Eq (8), for instance, it is important to know that $SiCl_4$ is able to donate about two Cl groups to magnesium hydrocarbyl compounds.

Another critical aspect of this invention, is the ability of the above strategy to produce a material which detailed chemical characterization shows to be a solid, magnesium, halide and hydrocarbyloxide containing material of uniform composition and purity, and not a mixture of, e.g. $MgCl_2$ and $Mg(OR)_2$ which would merely have the correct average composition.

Another interesting aspect of this invention is that the selectivity of the reactions, and the flexibility in amounts used, makes it possible to prepare solids of uniform composition and purity with previously unanticipated component ratios: i.e. with Cl:Mg:OEt ratios other than 1:1:1, such as $Cl_3Mg_2(OEt)$. Consequently, this strategy makes available a whole range of discrete magnesium compounds, with a variety of compositions, that are useful as catalyst supports.

The Examples shown below demonstrate that it is possible to use selective reactions to prepare substantially pure solids of uniform purity and composition containing chlorine, magnesium and ethoxide. Examples 3 and 5 demonstrate the preparation of substances with empirical formulae: ClMgOEt and Cl$_3$Mg$_2$(OEt), respectively. Example 6 demonstrates that, when sufficiently selective components are used, intermediate amounts of the components lead to simple mixtures of the possible products. These results are a large improvement over the prior art, where complex mixtures are more typical, substantially pure solids of uniform composition and purity are not obtained.

Figure 2:
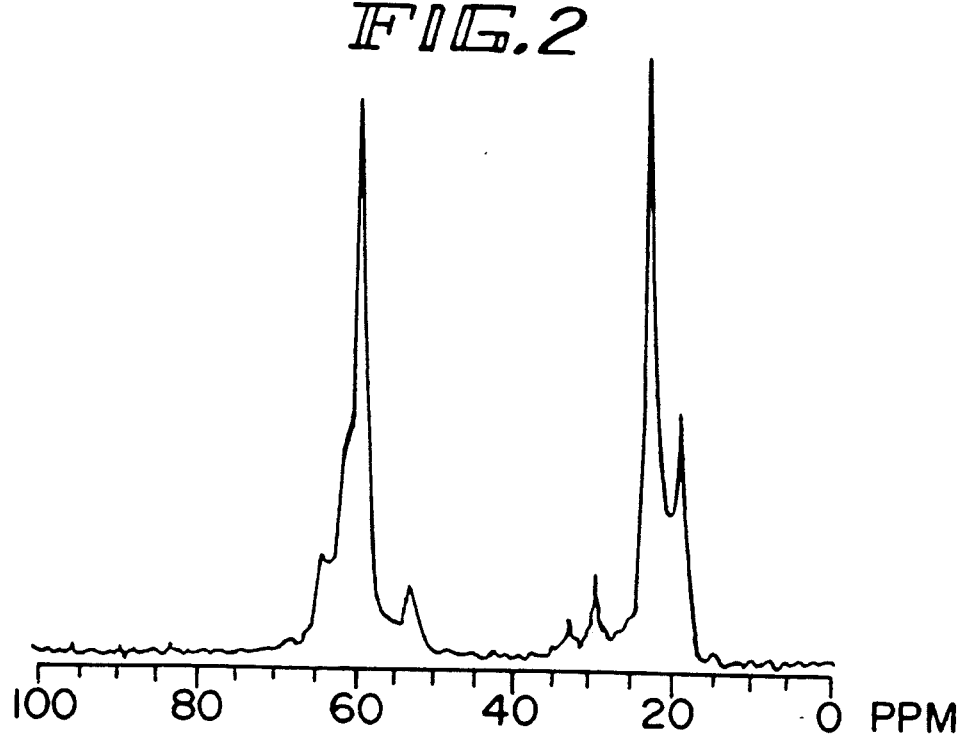

The purity and compositional uniformity of the products formed by the present invention can be confirmed by solid state $^{13}$C nuclear magnetic resonance spectroscopy. The instant products show no more than one strong, narrow absorption peak for each chemically inequivalent carbon atom in the hydrocarbyloxy ligand therein. For example, FIG. 1 illustrates the spectra for ClMg(OEt) made in accordance with the present invention, whereas FIG. 2 illustrates the distinctly differing spectra, not containing strong narrow absorption peaks, for the type of material claimed to be ClMg(OEt) as made in Example 1 of U.S. Pat. No. 4,820,879.

Example 7A shows that if a physical mixture of MgCl$_2$ and Mg(OEt)$_2$ is prepared, $^{13}$C CPMAS NMR can be used to establish that Mg(OEt)$_2$ is present. Example 7B shows that $^{13}$C CPMAS NMR has sufficient resolution to differentiate between Cl$_3$Mg$_2$OEt, as prepared in Example 5, and Mg(OEt)$_2$.

Examples 8 through 11 demonstrate use of the present invention to prepare materials containing alkoxy groups containing aryl moieties. While the processes of Examples 9 and 11 have not been optimized and the products formed have not been completely analyzed or purified, the results obtained are sufficient to demonstrate successful use of the invention in making the intended product. In both cases, a ClMgOR compound was formed which had spectral characteristics indicative of a single type of ClMgOR product (versus a mixture of many products as in the prior art) which was spectroscopically distinct from the corresponding Mg(OR)$_2$ compound, thereby ruling out formation of a mixture of MgCl$_2$ and Mg(OR)$_2$.

The present invention is further illustrated by the Examples which follow.

COMPARATIVE EXAMPLE 1

Preparation of Mg(OEt)$_2$ for Comparison Purposes

A 3-neck round bottom flask equipped with a mechanical stirrer, a reflux condenser and a gas inlet/outlet adapter was charged with butylethylmagnesium (130 g of a 20.2 wt % solution in heptane: 0.24 mole) and heptane (125 g). This solution was stirred (400 rpm) and was heated to reflux with an external oil bath. Heating was discontinued while tetraethyl orthosilicate (49.9 g, 0.24 mole) was added at a rate just sufficient to maintain reflux. Near the end of the addition, precipitates began to form. Heating was resumed, and the solution was refluxed for two additional hours. The solvent and volatiles were removed in vacuo to give colorless solid Mg(OEt)$_2$ (32.9 g, theory=27.7 g).

Solid state $^{13}$C CPMAS and inverse-gated decoupled MAS NMR spectra of this product are dominated by two resonances corresponding to carbons in the ethoxy groups. These resonances accounted for ca. 85% of the signal intensity in the $^{13}$C inverse-gated decoupled MAS NMR spectrum. The remaining 15% of signal intensity was shared among several peaks that could be assigned to heptane and/or hydrocarbyl groups bound to silicon. $^{29}$Si CPMAS NMR showed the presence of silicon compounds of the type: R$_x$Si(OEt)$_{4-x}$ 0≦x<4.

The $^{13}$C CPMAS NMR spectrum of this product, and that of a commercial sample of Mg(OEt)$_2$ (Aldrich Chemical Co.) were both characterized by two resonances: one corresponding to the methylene ($\delta$=58.1 ppm) carbon, and the other to the methyl ($\delta$=21.7 ppm) carbon of the ethoxy group.

The x-ray powder diffraction pattern for this material showed prominent lines at d=8.26 and 4.17 Å, with the lowest angle reflection at d=9.82

COMPARATIVE EXAMPLE 2

Preparation of MgCl$_2$ for Comparison Purposes

A 3-neck round bottom flask equipped with a mechanical stirrer, a reflux condenser, and a gas inlet/outlet was charged with butylethylmagnesium (104.6 g of 20.2 wt % solution in heptane: 0.19 mole) and heptane (109 g). This solution was cooled to −15° C. and stirred at 200 rpm. Silicon tetrachloride (32.5 g, 0.19 mole) was added. No reaction or exotherm was observed upon addition of SiCl$_4$. The solution temperature was increased by about 1° C./minute until refluxing was achieved. After an hour, the reaction mixture was cooled and precipitated solids were allowed to settle. The supernate was decanted, the solids were washed with three 200 ml portions of fresh heptane and were then collected by filtration (17.5 g, 96% of theory).

The product contained less than 0.2% alkanes by headspace GC analysis and showed only traces of carbon and silicon in $^{13}$C and $^{29}$Si CPMAS NMR analyses. Acid-base titration showed no basic components. Elemental analysis showed 25.6% Mg and 72.4% Cl (theory: 25.5% Mg, 74.4% Cl). The X-ray powder diffraction pattern of this material matched the known pattern for MgCl$_2$. The product had a surface area of 12 m$^2$/g and a median particle size of 12 $\mu$.

The x-ray powder diffraction pattern for this material showed prominent lines at d=4.15 and 2.58 Å, with the lowest angle reflection at 8.26 Å.

EXAMPLE 3

Preparation of High Surface Area ClMg(OEt)

A 1 L, 3-neck, round bottom flask equipped with a mechanical stirrer, a reflux condenser, and a gas inlet/outlet was charged with butylethylmagnesium (208.2 g of 20.2 wt % Mg/Al solution in heptane: 0.38 mole) and heptane (130 g). This solution was stirred rapidly (400 rpm), heated to 60° C., and absolute ethanol (22.9 g, 0.50 mole) added slowly, using care to maintain the temperature. External heat was then increased to reflux the solvent. After two and one-half hours 0.38 mole of (Bu,Et)$_{0.7}$Mg(OEt)$_{1.3}$ was obtained in the form of a homogeneous solution.

The reaction solution was then cooled to −15° C. and stirred at 110 rpm. Silicon tetrachloride (31.6 g, 0.19 mole) was then added. No immediate exotherm or reaction was observed. The solution temperature was increased by about 1° C./minute to 58° C. where it was held for 16 hours. The reaction mixture was cooled, solids allowed to settle, and the supernate decanted. The solids were then washed with 2 300 mL portions of fresh solvent, collected by decantation and vacuum dried. 33.9 g of solid product were obtained (82% recovery of Mg using a Mg content of 22.4%).

$^{13}$C CPMAS NMR analysis of this product showed it to have two sharp resonances, corresponding to a single methylene ($\delta$=59.3 ppm) and a single methyl ($\delta$=19.7 ppm) carbon signal characteristic of a material containing only one ethoxy group environment. Some very weak signals, not associated with ethoxy groups bound to magnesium, probably due to residual heptane or silicon hydrocarbyl groups, were also present.

The X-ray powder diffraction pattern for this material showed prominent lines at d=9.30 and 4.17 Å, with the lowest angle reflection at 9.30 Å.

Elemental analysis showed that this product contained 22.4% Mg and 31.9% Cl along with 5.20% H, 24.35% C. The ratio of Cl to Mg was 0.98:1. Acid-base titration of this material shows that it contains 9.4 mmoles base/gram solid. The ratio of (OEt) groups (total base) to Mg was 1.02 to 1. The sum of the Mg, Cl, C and H analyses, added to the amount of oxygen required by the base analysis totals 98.9%.

BET surface area analysis of this product found 233 m$^2$/g. The isothermal desorption curve did not show hysteresis. N$_2$ porosimetry fond a pore volume of 0.33 cc/g at P/P$_o$=0.98. SEM examination of the product showed it to be composed of agglomerates of submicron sized globular particles. Particle size analysis of this product showed a median particle size of the agglomerates of 59 $\mu$.

EXAMPLE 4

Preparation of Low Surface Area ClMg(OEt)

A 1 L, 3-neck, round bottom flask equipped with a mechanical stirrer, a reflux condenser, and a gas inlet/outlet was charged with butylethylmagnesium (135.8 g of 20.2 wt % solution in heptane: 0.25 mole) and heptane (149 g). This solution was stirred rapidly (400 rpm), heated to 60 °C., and absolute ethanol (13.2 g, 0.29 mole) added slowly, using care to maintain the temperature. External heat was then increased to reflux the solvent. After three hours 0.25 mole of (Bu,Et)$_{0.85}$Mg(OEt)$_{1.15}$ was obtained in the form of a homogeneous solution.

The reaction solution was then cooled to −15° C. and stirred at 110 rpm. Silicon tetrachloride (21.7 g, 0.13 mole) was then added. No immediate exotherm or reaction was observed. The solution temperature was increased by about 1° C./minute to 58° C. where it was held for 15 hours. The reaction mixture was cooled, solids allowed to settle, and the supernate decanted. The solids were then washed with 3 300 mL portions of fresh solvent, collected by filtration and vacuum dried.

$^{13}$C CPMAS NMR analysis of this product showed it to have two sharp resonances, corresponding to a single methylene ($\delta$=59.3 ppm) a single methyl ($\delta$=19.7 ppm) carbon signal characteristic of a material containing only one ethoxy group environment. Weak signals corresponding to a low levels of a higher Cl content material (i.e. the product from example 5) are also present.

The X-ray powder diffraction pattern from this product, which was different from that of known materials, showed several lines, the most prominent corresponding to a d-spacing of 9.30 Å. The X-ray powder diffraction pattern of this material showed no evidence of MgCl$_2$.

Elemental analysis showed that this product contained 21.6% Mg and 33.4% Cl along with 5.06% H, 23.41% C. The ratio of Cl to Mg was 1.06:1. Acid-base titration of this material shows that it contains 9.2 mmoles base/gram solid. The ratio of (OEt) groups (total base) to Mg was 1.04 to 1. The sum of the Mg, Cl, C and H analyses, added to the amount of oxygen required by the base analysis totals 98.2%.

BET surface area analysis of this product found 6.1 m$^2$/g. SEM examination of the product showed it to be composed of irregular smooth surfaced particles from 0.5 to 10 $\mu$ in size. Particle size distribution analysis found a median particle size of 14 $\mu$.

EXAMPLE 5

Preparation of Novel, High Surface Area Cl$_3$Mg$_2$(OEt)

A 1 L 3-neck round bottom flask equipped with a mechanical stirrer, a reflux condenser, and a gas inlet/outlet port, was charged with butylethylmagnesium (159.8 g of a 20.2 wt % solution in heptane: 0.29 mole) and heptane (130 g). The solution was stirred rapidly (400 rpm), heated to 50 °C., and absolute ethanol (8.1 g, 0.18 mole) added slowly, causing the temperature to rise to 60° C. This temperature was maintained during the ethanol addition. External heat was then applied to reflux the solvent. After two hours 0.29 mole of R$_{1.2}$Mg(OEt)$_{0.8}$ was obtained in the form of a homogeneous solution.

The reaction solution was then cooled to −15° C. and stirred at 150 rpm. Silicon tetrachloride (39.4 g, 0.23 mole) was then added. No immediate exotherm or reaction was observed. The solution temperature was increased by about 1° C./minute to 60° C. where it was held for 12 hours. The reaction mixture was cooled, solids allowed to settle, and the supernate decanted. The solids were then washed with 5 200 mL portions of fresh solvent, collected by filtration and vacuum dried. The yield of solid product was 25.3 g (80.1% recovery of Mg using a Mg content of 22.0%).

$^{13}$C CPMAS NMR analysis of this product showed it to have two sharp resonances, corresponding to a single methylene ($\delta$=63.0 ppm) carbon signal, and a single methyl ($\delta$=18.9 ppm) carbon signal, which is characteristic of a material containing only one ethoxy group environment. Signals from a small amount of residual heptane were also present.

The X-ray powder diffraction pattern for this material showed prominent lines at d=4.17 and 8.66 Å, with the lowest angle reflection at d=9.93 Å.

Elemental analysis showed that this product contained 22.5% Mg and 49.1% Cl along with 3.40% H, 14.88% C. The ratio of Cl to Mg was 1.50:1. Acid-base titration of this material shows that it contains 5.12 mmoles base/gram solid. The ratio of (OEt) groups (total base) to Mg was 0.55 to 1. The sum of the Mg, Cl, C and H analyses, added to the amount of oxygen required by the base analysis totals 98.3%. 5 BET surface area analysis of this product found 299 m$^2$/g. N$_2$ porosimetry found a pore volume of 0.42 cc/g at P/P$_o$=0.98. SEM examination of the product showed it to be composed of irregularly shaped, porous, agglomerates from 5 to 100 $\mu$ in size. Particle size distribution analysis found a median particle size of 35.3 $\mu$.

EXAMPLE 6

Preparation of a Mixture of ClMg(OE) and Cl$_3$Mg$_2$(OEt)$_1$

A 1 L, 3-neck, round bottom flask equipped with a mechanical stirrer, a reflux condenser, and a gas inlet/outlet Was charged with butylethylmagnesium (162.6 g of 20.2 Wt% solution in heptane: 0.30 mole) and heptane (200 g). This solution was stirred rapidly (400 rpm), and absolute ethanol (14.1 g, 0.31 mole) added slowly, causing a rise in temperature to 60 °C. External heat was then applied to reflux the solvent. After three hours 0.30 mole of $R_{1.0}Mg(OEt)_{1.0}$ was obtained in the form of a homogeneous solution.

The reaction solution was then cooled to −15° C. and stirred at 110 rpm. Silicon tetrachloride (24.9 g, 0.15 mole) was then added. No immediate exotherm or reaction was observed. The solution temperature was increased by about 1° C./minute to solvent reflux, where it was held for 2 hours. The reaction mixture was cooled, solids allowed to settle, and the supernate decanted. The solids were then washed with 2 300 mL portions of fresh solvent, collected by filtration and vacuum dried. The yield of solid product was 26.4 g (80% recovery of Mg using a Mg content of 22.2%).

$^{13}$C CPMAS NMR analysis of this product showed it to be a mixture of the products from Examples 3 (main component) and 5. Some very weak signals, not associated with ethoxy groups bound to magnesium, probably due to residual heptane or silicon hydrocarbyl groups, were also present.

Elemental analysis showed that this product contained 22.2% Mg and 36.8% Cl along with 5.05% H, 22.75% C and 0.14% Si. The ratio of Cl to Mg was 1.14:1. Acid-base titration of this material shows that it contains 7.9 mmoles base/gram solid. The ratio of (OEt) groups (total base) to Mg was 0.87:1. The sum of the Mg, Cl, C, H and Si analyses, added to the amount of oxygen required by the base analysis totals 99.6%.

BET surface area analysis of this product found 60 m$^2$/g, with some hysteresis in the isothermal desorption curve characteristic of 'ink-bottle' shaped pores present. $N_2$ porosimetry found a pore volume of 0.84 cc/g at $P/P_o = 0.98$. Particle size distribution analysis found a median particle size of 25 μ.

EXAMPLE 7

Mixture A: Equal amounts of $MgCl_2$ and $Mg(OEt)_2$ were ground together with a mortar and pestle, to prepare a physical mixture. The $^{13}$C CPMAS NMR spectrum of this mixture had peaks with the same chemical shift and shape as that of pure $Mg(OEt)_2$ (methylene $\delta = 58.1$ ppm, methyl $\delta = 21.7$ ppm).

Mixture B: One part of $Mg(OEt)_2$ was added to 4 parts $Cl_3Mg_2OEt$ as prepared by Example 5 and the resultant mixture ground with a mortar and pestle, to prepare an intimate physical mixture. The $^{13}$C CPMAS NMR spectrum of this mixture showed peaks from both components, having essentially the same chemical shift and shape as that of the pure compounds: $Mg(OEt)_2$ (methylene $\delta = 58.0$ ppm, methyl $\delta = 21.8$ ppm) and $Cl_3Mg_2OEt$ according to Example 3 (methylene $\delta = 63.3$ ppm, methyl $\delta = 19.2$ ppm).

COMPARATIVE EXAMPLE 8

Preparation of $Mg(-OC_6H_4CH)_2$ for Comparison Purposes

A 3-neck round bottom flask equipped with a mechanical stirrer, a reflux condenser and a gas inlet/outlet adapter was charged with para-cresol (9.32 g, 0.0862 mole) and heptane (60 g). Butylethylmagnesium (4.65 grams, 0.0421 mole) in n-heptane (124 g) was slowly added to the reaction flask and white precipitates formed immediately. The reaction mixture was then refluxed for 2 hours. The solids were filtered and then dried in vacuo to give 6.0 g of a colorless solid $Mg(-OC_6H_4CH_3)_2$ (57% recovery of Mg using a Mg content of 9.8%).

Elemental analysis showed 9.8% Mg. GC analysis after hydrolysis showed 90.4% para-cresol. The ratio of $(-OC_6H_4CH_3):MG$ was 2.1:1.0 and the sum of the magnesium and para-cresol analyses was 100.2%.

The solid state $^{13}$C CPMAS NMR spectrum of this product was characterized by four resonances: three resonances corresponding to aryl ($\delta_1 = 155.6$ ppm, $\delta_2 \approx \delta_3 = 130.6$ ppm, $\delta_4 = 117.1$ ppm) carbons, and one resonance corresponding to a methyl ($\delta_5 = 18.1$ ppm) carbon.

EXAMPLE 9

Preparation of $ClMg(OC_6H_4CH_3)$

A 3-neck round bottom indented flask equipped with a mechanical stirrer, a reflux condenser, and a gas inlet/outlet adapter was charged with butylethylmagnesium(292.7 g of 5.4 wt % solution in toluene: 0.143 mole). The solution was stirred rapidly (300 rpm), heated to 60° C., and para-cresol(15.47 g, 0.143 mole) added slowly. External heat was then increased to reflux the solvent. After 17 hours, silicon tetrachloride(12.42 g, 0.073 mole) was added slowly to the reaction mixture. Gelation occurred immediately upon the addition. The mixture was cooled with stirring to room temperature and then filtered. The solids were washed with 3 ×100 ml of n-heptane and vacuum dried. 11.58 g of solid colorless solid product were obtained (45% recovery of Mg using a magnesium content of 13.6%).

Elemental analysis showed 13.6% Mg and 14.2% Cl. GC analysis after hydrolysis showed 58.2% para-cresol. The ratio of $(-OC_6H_4CH_3):MG:Cl = 0.96:1.0:0.72$.

The solid state $^{13}$C CPMAS NMR spectrum of this product was characterized by four resonances: three resonances corresponding to aryl ($\delta_1 = 155.7$ ppm, $\delta_2 \approx \delta_3 = 130.1$ ppm, $\delta_4 = 119.1$ ppm) carbons, and one resonance corresponding to a methyl ($\delta_5 = 20.4$ ppm) carbon. Some signals, not associated with para-cresoxy groups bound to magnesium, probably due to residual n-heptane, magnesium hydrocarbyl groups, or silicon hydrocarbyl groups, were also present.

COMPARATIVE EXAMPLE 10

Preparation of $[Mg(OC_6H_2(C_4H_9)_2CH_3)_2]_2$

A 3-neck round bottom flask equipped with a mechanical stirrer, a reflux condenser and a gas inlet/outlet adapter was charged with 2,6-di-tert-butyl-4-methyl-phenol (99.5 g of a 49 wt % solution in n-heptane: 0.2201 moles). Butylethylmagnesium (128.4 g of a 9.5 Wt% solution in n-heptane: 0.1104 moles) was slowly added to the reaction flask. The reaction mixture was then refluxed for 2 hours. The soluble mixture was then allowed to cool to room temperature with stirring. The solids were filtered and then dried in vacuo to give 39.1 g of a colorless solid $[Mg(OC_6H_2(C_4H_9)_2CH_3)_2]_2$ (83% recovery based on a Mg content of 5.7%).

Elemental analysis showed 5.7% Mg. GC analysis after hydrolysis showed 93.9% 2,6,-di-tert-butyl-4-methylphenol. The ratio of $-OC_6H_2(C_4H_9)_2CH_3:Mg$ was 1.8:1.0 (the sum of the Mg and 2,6-di-tert-butyl-4-methylphenol analyses was 99.6%).

The solid state $^{13}$C CPMAS NMR spectrum of this product was characterized by fifteen resonances: eight resonances corresponding to aryl ($\delta_1 = 158.9$ ppm, $\delta_2 = 153.0$ ppm, $\delta_3 = 137.0$ ppm, $\delta_4 = 131.1$ ppm, $\delta_5 = 128.4$ ppm, $\delta_6 = 126.3$ ppm, $\delta_7 = 125.3$ ppm, $\delta_8 = 122.0$ ppm) carbons, and seven resonances corresponding to hydrocarbyl ($\delta_9 = 35.9$ ppm, $\delta_{10} = 35.2$ ppm, $\delta_{11} = 34.3$ ppm, $\delta_{12} = 31.8$ ppm, $\delta_{13} = 23.2$ ppm, $\delta_{14} = 21.5$ ppm, $\delta_{15} = 19.1$ ppm) carbons. The resonance pairs are indicative of a dimeric molecular structure, e.g. [Mg(OC$_6$H$_2$(C$_4$H$_9$)$_2$CH$_3$)$_2$]$_2$, which is typical for sterically crowded bis phenoxy magnesium compounds such as this (Inorganic Chemistry, Vol. 27 (1988), pp. 867-870).

EXAMPLE 11

Preparation of ClMg(OCH$_2$(C$_4$H$_9$)$_2$CH$_3$)

A 3-neck round bottom indented flask equipped with a mechanical stirrer, a reflux condenser, and a gas inlet/outlet adapter was charged with butylethylmagnesium(267 g of 6.55 wt % solution in toluene: 0.159 mole). The solution was stirred rapidly (300 rpm), heated to 60° C., and 2,6-di-tert-butyl-4-methylphenol (188.0 g of 24.2 wt % solution in toluene: 0.206 mole) was added slowly. External heat was then increased to reflux the solvent. The soluble mixture was heated at reflux for 2 hours and then cooled to −15° C. Silicon tetrachloride(13.91 g, 0.082 mole) was added slowly to the reaction mixture. The soluble mixture was heated at reflux for 1 hour and then cooled with stirring (400-500 rpm) to room temperature. The precipitate was filtered, washed with 100 ml of n-heptane and vacuum dried. 12.6 g of solid colorless solid product were obtained (26% recovery of Mg using a magnesium content of 8.0%).

Elemental analysis showed 8.0% Mg and 9.5% Cl. GC analysis after hydrolysis showed 75.5% 2,6-di-tert-butyl-4-methyl-phenol. The molar ratio of ($^-$OC$_6$H$_2$(C$_4$H$_9$)$_2$CH$_3$):Mg:Cl was 1.04:1.0:0.81.

The solid state $^{13}$C CPMAS NMR spectrum of this product was characterized by seven resonances: four resonances corresponding to aryl ($\delta_1 = 153.4$ ppm, $\delta_2 = 138.1$ ppm, $\delta_3 = 132.8$ ppm, $\delta_4 = 127.7$ ppm) carbons, and three resonances corresponding to hydrocarbyl ($\delta_5 = 35.7$ ppm, $\delta_6 = 31.7$ ppm, $\delta_7 = 20.6$ ppm) carbons.

The foregoing Examples have been presented for illustrative purposes only and, for that reason, should not be construed in a limiting sense. The scope of protection sought is set forth in the claims which follow.

We claim:

1. A process for the preparation of a substantially pure halomagnesium hydrocarbyloxide composition which comprises:
   (a) Reaction of a dihydrocarbylmagnesium compound with a compound reactive therewith which is capable of adding an hydrocarbyloxy functionality to the magnesium of the dihydrocarbylmagnesium with displacement of an hydrocarbyl functionality therefrom; and
   (b) thereafter reacting the product from (a) with a compound capable of adding an halogen functionality to the magnesium of the product from (a) with displacement of the remaining hydrocarbyl functionality.

2. A process as claimed in claim 1 wherein the halogen is chlorine.

3. A process as claimed in claim 1 wherein the dihydrocarbylmagnesium is butylethylmagnesium.

4. A process as claimed in claim 1 wherein the compound reactive with the dihydrocarbylmagnesium used in step (a) is an alcohol.

5. A process as claimed in claim 2 wherein the compound reactive with the dihydrocarbylmagnesium used in step (a) is an alcohol.

6. A process as claimed in claim 3 wherein the compound reactive with the dihydrocarbylmagnesium used in step (a) is an alcohol.

7. A process as claimed in claim 3 wherein the compound reactive with the dihydrocarbylmagnesium used in step (a) is an alcohol and the halogen is chlorine.

8. A process as claimed in claim 7 wherein the compound reactive with the dihydrocarbylmagnesium used in step (a) is ethanol and the halogen is chlorine.

9. A substantially pure halomagnesium hydrocarbyloxide formed by the process of claim.

10. A substantially pure halomagnesium hydrocarbyloxide formed by the process of claim 2.

11. A substantially pure halomagnesium hydrocarbyloxide formed by the process of claim 3.

12. A substantially pure halomagnesium hydrocarbyloxide formed by the process of claim 4.

13. A substantially pure halomagnesium hydrocarbyloxide formed by the process of claim 5.

14. A substantially pure halomagnesium hydrocarbyloxide formed by the process of claim 6.

15. A substantially pure halomagnesium hydrocarbyloxide formed by the process of claim 7.

16. A substantially pure halomagnesium hydrocarbyloxide formed by the process of claim 8.

17. A substantially pure, chemically distinct, halomagnesium hydrocarbyloxide compound having a $^{13}$C nuclear magnetic resonance spectrum exhibiting no more than one strong, narrow absorption peak for each chemically inequivalent carbon atom in the hydrocarbyloxy ligand of the compound.

18. A compound as claimed in claim 17 comprising ethoxide as the hydrocarbyloxide moiety.

19. A compound as claimed in claim 18 comprising chlorine as the halogen.

20. A compound as claimed in claim 19 wherein the ratio of chlorine to magnesium to ethoxide is 1 to 1 to 1.

21. A compound as claimed in claim 19 wherein the ratio of chlorine to magnesium to ethoxide is 3 to 2 to 1.

* * * * *